(12) United States Patent
Dickow et al.

(10) Patent No.: US 9,952,124 B2
(45) Date of Patent: Apr. 24, 2018

(54) SYSTEM FOR TAKING EXHAUST GAS SAMPLES FROM INTERNAL COMBUSTION ENGINES

(71) Applicant: AVL EMISSION TEST SYSTEMS GMBH, Neuss (DE)

(72) Inventors: Achim Dickow, Velbert (DE); Rainer Ballik, Moers (DE); Sascha Willich, Kaarst (DE)

(73) Assignee: AVL EMISSION TEST SYSTEMS GMBH, Neuss (DE)

( * ) Notice: Subject to any disclaimer, the term of this patent is extended or adjusted under 35 U.S.C. 154(b) by 621 days.

(21) Appl. No.: 14/384,690

(22) PCT Filed: Mar. 12, 2013

(86) PCT No.: PCT/EP2013/054973
§ 371 (c)(1),
(2) Date: Sep. 12, 2014

(87) PCT Pub. No.: WO2013/135678
PCT Pub. Date: Sep. 19, 2013

(65) Prior Publication Data
US 2015/0020582 A1 Jan. 22, 2015

(30) Foreign Application Priority Data
Mar. 14, 2012 (DE) .................. 10 2012 102 137

(51) Int. Cl.
*G01M 15/10* (2006.01)
*G01N 1/22* (2006.01)
*G01N 33/00* (2006.01)

(52) U.S. Cl.
CPC ........ *G01N 1/2252* (2013.01); *G01M 15/102* (2013.01); *G01N 33/0018* (2013.01); *G01N 2001/2255* (2013.01)

(58) Field of Classification Search
CPC ..................................................... G01N 1/2252
(Continued)

(56) References Cited

U.S. PATENT DOCUMENTS 3,817,100 A    6/1974  Anderson et al.
3,986,386 A   10/1976  Beltzer et al.
(Continued)

FOREIGN PATENT DOCUMENTS

AT           11700 E      6/1985
CN         87207061 U    12/1987
(Continued)

*Primary Examiner* — Herbert K Roberts
(74) *Attorney, Agent, or Firm* — Norman B. Thot

(57) ABSTRACT

A system for taking exhaust gas samples from internal combustion engines includes an exhaust gas duct comprising an outflow cross section and an exhaust gas inlet. The exhaust gas duct communicates with an exhaust gas source via the exhaust gas inlet. An air duct takes in ambient air via a filter. The outflow cross section is concentric in the air duct. A mixing zone is arranged downstream of the outflow cross section. A dilution tunnel has an exhaust gas/air mixture flow therethrough. An annular orifice is arranged downstream of the outflow cross section in the dilution tunnel. A flow deflection device is arranged upstream of the annular orifice and downstream of the outflow cross section. The flow deflection device deflects the exhaust gas/air mixture so that it departs from a center axis of the dilution tunnel immediately downstream of the flow deflection device in an axially symmetrical manner.

16 Claims, 2 Drawing Sheets

(58) Field of Classification Search
USPC .................................. 366/175.2, 173.2, 338
See application file for complete search history.

(56) References Cited

U.S. PATENT DOCUMENTS

| | | | |
|---|---|---|---|
| 5,090,258 A | 2/1992 | Yamasaki et al. | |
| 5,469,731 A | 11/1995 | Decker et al. | |
| 7,191,671 B2 | 3/2007 | Kreft | |
| 7,555,928 B2 | 7/2009 | Silvis | |
| 7,559,262 B2 | 7/2009 | Silvis et al. | |
| 2003/0172741 A1* | 9/2003 | Busch | G01N 1/2252 73/861.21 |
| 2003/0205096 A1* | 11/2003 | Gehner | B01F 3/02 73/863 |
| 2004/0226354 A1 | 11/2004 | Schmidt | |
| 2005/0089408 A1* | 4/2005 | Solomon | B01F 5/0413 417/182 |
| 2006/0245296 A1* | 11/2006 | Nishioka | B01D 53/8631 366/174.1 |
| 2008/0066565 A1 | 3/2008 | Silvis et al. | |
| 2011/0252864 A1 | 10/2011 | Guenther et al. | |
| 2012/0036836 A1 | 2/2012 | Dickow | |

FOREIGN PATENT DOCUMENTS

| | | |
|---|---|---|
| DE | 690 21 836 T2 | 2/1996 |
| DE | 10 2009 015 188 A1 | 10/2010 |
| EP | 0 042 800 A1 | 12/1981 |
| EP | 0 428 850 A1 | 5/1991 |
| EP | 1 477 801 A1 | 11/2004 |
| JP | 4-13640 U | 2/1992 |
| JP | 4-72542 A | 3/1992 |
| JP | 6-294718 A | 10/1994 |
| JP | 2536681 B2 | 9/1996 |
| KR | 1992-0010292 B1 | 11/1992 |
| WO | WO 2005/045398 A1 | 5/2005 |

* cited by examiner

SYSTEM FOR TAKING EXHAUST GAS SAMPLES FROM INTERNAL COMBUSTION ENGINES

CROSS REFERENCE TO PRIOR APPLICATIONS

This application is a U.S. National Phase application under 35 U.S.C. § 371 of International Application No. PCT/EP2013/054973, filed on Mar. 12, 2013 and which claims benefit to German Patent Application No. 10 2012 102 137.6, filed on Mar. 14, 2012. The International Application was published in German on Sep. 19, 2013 as WO 2013/135678 A1 under PCT Article 21(2).

FIELD

The present invention relates to a system for taking exhaust gas samples from internal combustion engines having an exhaust gas duct which is in fluid communication with an exhaust gas source via an exhaust gas inlet, an air duct into which ambient air is adapted to be taken in via an air filter, a mixing zone which is arranged downstream of a flow cross section of the exhaust air duct, a dilution tunnel through which an exhaust gas/air mixture flows, wherein an outflow cross section of the exhaust gas duct is arranged essentially concentrically in the air duct, and downstream of the outflow cross section of the exhaust gas duct an annular orifice is arranged in the dilution tunnel.

BACKGROUND

Such systems are known as CVS system (constant volume sampling). In these systems, air is mixed into the exhaust gas in an amount so as to produce a constant volume flow of the air/exhaust gas mixture. The samples taken by these systems are collected in bags and are then analyzed with regard to their pollutant content. The carbon dioxide content, the carbon monoxide content, the hydrocarbon content, the nitrogen oxide content, as well as the particle load are measured. The type of measurement is regulated by law, for example, by the ECE Guideline R. 83 for the European Community countries, or the Code of Federal Regulations, Act No. 40, for the United States.

DE 10 2009 015 188 A1 describes a system for taking exhaust gas samples which is adapted to be connected to two different exhaust gas sources so that one system can measure both the particle load of diesel engines and that of petrol engines. The exhaust gas duct of the system extending from the diesel engine concentrically ends in the air duct upstream of an orifice. A mixing zone is created in which the exhaust gas is mixed with the air in the region between the outflow cross section of the exhaust gas duct and the orifice.

It has turned out, however, that steaks may occur in such a system flow in which the exhaust gas is not as effectively mixed as in other regions. A uniform mixing is thus not provided despite relatively long run lengths so that measuring results may be falsified.

SUMMARY

An aspect of the present invention is to develop a system with which a representative sampling in accordance with the legal regulations is provided by preventing regions of poor exhaust gas mixing from being created. An alternative aspect of the present invention is to provide a system which can be manufactured and operated at low cost with feed pumps having a relatively small capacity which should suffice for feeding the two gas flows.

In an embodiment, the present invention provides a system for taking an exhaust gas sample from an internal combustion engine which includes an exhaust gas duct comprising an outflow cross section and an exhaust gas inlet. The exhaust gas duct is configured to be in a fluid communication with an exhaust gas source via the exhaust gas inlet. An air duct is configured to take in ambient air via an air filter. The outflow cross section of the exhaust gas duct is arranged so as to be substantially concentric in the air duct. A mixing zone is arranged downstream of the outflow cross section. A dilution tunnel comprises a center axis. The dilution tunnel is configured to have an exhaust gas/air mixture flow therethrough. An annular orifice is arranged downstream of the outflow cross section in the dilution tunnel. A flow deflection device is arranged upstream of the annular orifice and downstream of the outflow cross section. The flow deflection device is configured to deflect the exhaust gas/air mixture so that a flow of the exhaust gas/air mixture departs from the center axis of the dilution tunnel immediately downstream of the flow deflection device in an axially symmetrical manner

BRIEF DESCRIPTION OF THE DRAWINGS

The present invention is described in greater detail below on the basis of embodiments and of the drawings in which.

DETAILED DESCRIPTION

Figure 1:
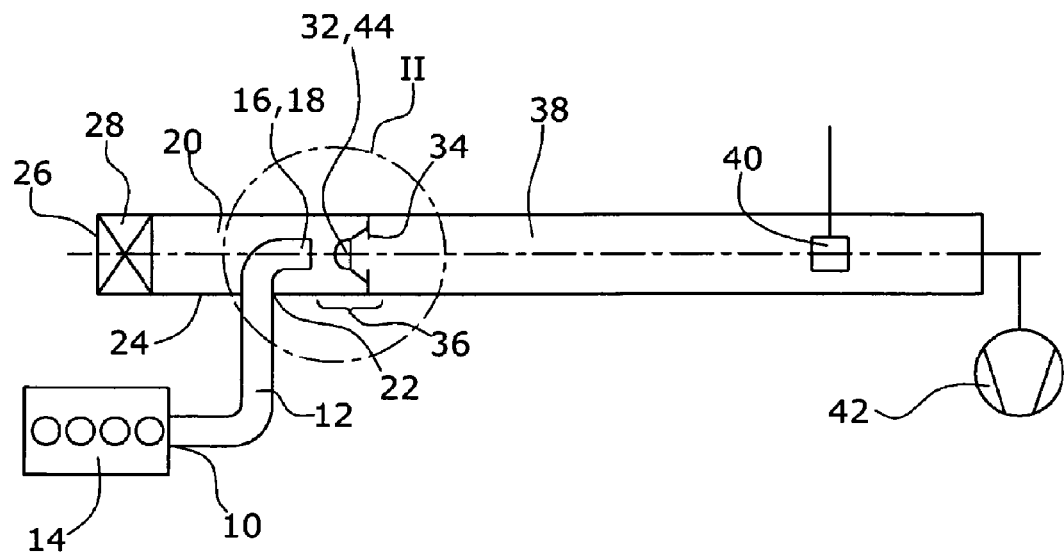
FIG. 1 shows a schematic side view of a system for taking exhaust gas samples according to the present invention.

Because a device is arranged upstream of the orifice and downstream of the outflow cross section of the exhaust gas duct via which the exhaust gas flow is deflected so that, immediately downstream of the device, the exhaust gas flow departs from the center axis of the dilution tunnel in an axially symmetrical manner, the exhaust gas is directly fed into the air flow which had previously been displaced into the outer region of the dilution tunnel by the exhaust duct projecting into the air duct, whereby the mixing effect is considerably increased. The orifice then increases the velocity of the exhaust gas/air mixture, whereby additional turbulences are created, which lead to an additional homogenization of the mixed flow.

In an embodiment of the present invention, the flow deflection device can, for example, be defined by a body comprising a spherical zone and being concentrically arranged in the dilution tunnel. Owing to the spherical zone, the pressure loss is not substantially increased when the exhaust gas flow is deflected so that the driving pressure gradient, and thus the power consumption of a feed pump, need not be increased. This body also allows for a particularly good mixing of the two gas flows to be achieved.

In an embodiment of the present invention, the spherical zone can, for example, be a hemisphere. This design produces particularly good results with regard to a homogenization of the mixture and the simultaneous reduction of the pressure loss.

The surface of the spherical zone is electropolished to prevent particles from depositing. Particles later detaching from the deflection device are further prevented from falsifying the measuring result.

In an embodiment of the spherical zone, said zone comprises a central hole. This hole prevents creation of a stagnation point which would considerably increase the pressure loss, without noticeably deteriorating the mixing effect.

The spherical zone or the orifice can, for example, further be adapted to be heated. This is realized by arranging a heating film on the downstream surface of the spherical zone or the orifice so the latter is not directly subjected to the exhaust gas flow, but is protected by the upstream surface. Formation of condensate on the surfaces across which the gas flows is thus prevented, which, in turn, results in a reduction of deposits.

Good results are achieved when the projection surface of the spherical zone in the direction of the center axis corresponds at least to the outflow cross section of the exhaust gas duct since this provides that the overall exhaust gas flow is deflected in the direction of the air flow and prevents an additional reduction of area which would lead to a pressure loss.

In an embodiment of the present invention, the flow cross section of the orifice can, for example, correspond to 1.2 to 1.8 times the cross section of the flow deflection device. The flow velocity is thus increased and turbulences are produced which further increase the mixing effect without resulting in excessive pressure losses.

In an embodiment of the present invention, the distance of the flow deflection device to the outflow cross section of the exhaust gas duct can, for example, be one third to one fifth of the difference between the cross section of the air duct and the cross section of the exhaust gas duct. It is thus provided that the pressure drop does not become excessively large when the exhaust gas flows into the air flow. An adequate outflow area is thus made available to the exhaust gas flow while the deflection angle is adequately large to produce turbulences so that a streak formation can be prevented.

When the gas flows through the orifice, an excessively large pressure drop is prevented in that the distance of the flow deflection device to the orifice is one third to one fifth of the cross section of the air duct. An adequate area for the exhaust gas/air mixture is thus made available while turbulences are produced due to the deflection occurring in close succession in opposite directions.

In an embodiment of the present invention, the flow deflection device is, for example, defined by a plurality of outflow pipes arranged symmetrically to each other relative to the center axis. The pressure drop is thus additionally reduced since no flow restrictor other than the orifice is arranged behind the exhaust gas duct. The exhaust gas flow is nonetheless deflected in the direction of the air flow.

In an embodiment of the present invention, four outflow pipes can, for example, be arranged offset from each other by 90°. This results in an adequately constant introduction of the exhaust gas across the overall cross section, but at low design expenditure. This embodiment is also easy to install.

In an embodiment of the present invention, in the immediate vicinity of the exhaust gas duct or in the exhaust gas duct, the four outflow pipes can, for example, at first extend parallel to the center axis, and in the further course outside the exhaust duct, they can, for example, continuously bend away from the center axis. Pressure losses are reduced due to this continuous bending.

In an embodiment of the present invention, the outflow cross sections of the outflow pipes can, for example, include an angle of 30° to 80° to the center axis of the dilution tunnel, whereby an adequate deflection for increasing the mixing effect is provided and the pressure drop is kept within acceptable limits when the two gas flows meet each other so that the overall pressure increase of the fans for feeding the gas flow need not be further adjusted.

A simple fastening and installation is provided when the flow deflection device is fastened with the aid of at least one, for example, of three holding fixtures to the orifice since the installation is carried out together with the installation of the orifice.

A system for taking exhaust gas samples from internal combustion engines is thus provided which provides that representative samples can be taken from the dilution tunnel because a very good mixing of the two gas flows is provided. The system is furthermore inexpensive to manufacture and operate since the installation is simple and relatively small transport blowers can be used because additional pressure losses are kept small.

Two exemplary embodiments of a system for taking exhaust gas samples according to the present invention are shown in the drawings and are described hereinafter.

The system according to the present invention for taking exhaust gas samples from internal combustion engines for diesel or petrol engines comprises an exhaust gas inlet 10 via which an exhaust gas duct 12 is in fluid communication with an exhaust gas source 14 which is defined by an internal combustion engine of a motor vehicle.

The exhaust gas duct 12 comprises an end 16 having an outflow cross section 18, the end 16 concentrically ending inside an air duct 20. For this purpose, the air duct 20 comprises an opening 22 in its boundary wall 24, through which opening 22 the exhaust gas duct 12 vertically projects into the air duct 20. In order to concentrically end in the air duct 20, the exhaust gas duct 12 is bent by 90°.

Upstream of the exhaust gas duct 12, the air duct 20 comprises an inlet 26 at which a first air filter 28, normally made up of three filters, is arranged via which air can be taken into the air duct 20. The bend of the exhaust air duct 12 is designed so that the outflow direction of the exhaust gas is directed to the side opposite to the first air filter 28 so that the air flow and the exhaust gas flow at the outflow cross section 18 of the exhaust gas duct 12 have a common flow direction which is essentially parallel to the center axis of the air duct 20.

Figure 2:
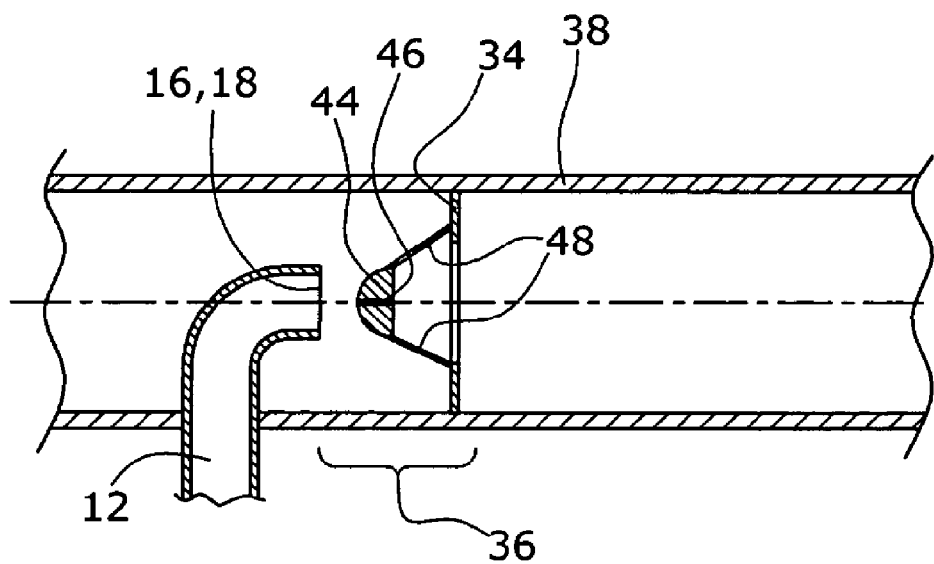
FIG. 2 shows an enlarged three-dimensional view of a section of the system of FIG. 1 in the region of the mixing zone.

As seen in the direction of flow, a flow deflection device 32 for deflecting the exhaust gas flow is arranged behind the outflow cross section 18 of the exhaust gas duct 12. This may be of different designs as will be learned from the following description of FIGS. 2 and 3. Regardless of the design of the flow deflection device 32, it is provided for deflecting the exhaust gas flow in the direction of the air flow, i.e., with a component in radial direction of the air duct 20, into the air flow, whereby turbulences are produced and mixing is improved.

An orifice 34 is arranged behind the flow deflection device 32 which narrows the free-flow cross section of the air duct 20 so that the flow velocity is increased and additional turbulence is produced. These turbulence zones define a mixing zone 36 in which the exhaust gas flow and the air flow are mixed as completely as possible and which extends up to a point behind the orifice 34.

A dilution tunnel 38 is provided adjacent to the mixing zone 36 in which a uniform flow of the exhaust gas/air mixture is present without any streaks forming. In the dilution tunnel 38, a sampling probe 40 for taking a sample from the mixed flow is arranged centrally to the center axis. The sample flow removed by the sampling probe 40 may be fed via a heatable particle filter to a flame ionization detector with the aid of which the hydrocarbons in the exhaust gas can be determined to establish the content of nitrogen oxides, carbon dioxide, and carbon monoxide in the exhaust gas. Via the sampling probe 40, the particle emissions are removed and fed to a particle measuring device. The analysis flows are respectively fed via separate pumps (not shown).

The remaining mixed gas flow travels from the dilution tunnel 38 to a controllable feed pump 42 which is provided for producing an adequate pressure for feeding the air and the exhaust gas. The mixed gas flow is here discharged. Besides provision of a controlled feed pump 42, it is also possible to arrange a venturi nozzle in front of the feed pump 42 for adjusting the desired flow rate.

It should further be appreciated that the gas flow through the feed pump 42 is measured at a constant temperature and a constant pressure and/or a constant volume flow. In any case, the exhaust gas is diluted with the ambient air at a defined ratio. The sampling takes place proportionally to the flow rate through the feed pump 42. Sampling systems with a variable dilution and a displacement pump are known as are dilution systems with a critical flow rate through a venturi pipe as described, for example, in ECE Guideline R. 83. The arrangement of the flow regulators, valves, flow, pressure and temperature measuring instruments used in these systems is also known and differs according to the systems used so that these possibilities of regulation are assumed to be expert knowledge. The present invention is suitable for all these types of sampling.

The sampling results of such a system are representative only if it is ensured that as homogeneous as possible a flow exists at the sampling points, i.e., adequate mixing of the exhaust gas flow into the air flow is provided and streak formation is reliably prevented. As has been mentioned above, this is realized in the present invention with the flow deflection device 32. In the embodiment shown in FIG. 2, this flow defection device 32 is defined by a body designed as a spherical zone, in the present case, a hemisphere 44 whose convex surface is directed in the direction of the exhaust gas duct 12.

This hemisphere 44 is located at a distance of 45 mm to the outflow cross section 18 of the exhaust gas duct 12 and has a diameter of approximately 95 mm, while the outflow cross section of the exhaust gas duct 12 is approximately 90 mm. The hemisphere 44 is in turn located at a distance of approximately 70 mm to the orifice 34 whose free-flow cross section is approximately 150 mm. These dimensions have been determined depending on the diameter of the air duct 20 which in the present case is 273 mm, so that the flow cross section of the orifice 34 corresponds to approximately 1.6 times the cross section of the flow deflection device 32, the distance of the flow deflection device 32 to the outflow cross section 18 of the exhaust gas duct 12 being approximately one quarter of the difference between the cross section of the air duct 20 and the cross section of the exhaust gas duct 12, and the distance of the flow deflection device 32 to the orifice 34 being approximately one quarter of the diameter of the air duct 20.

These aforementioned ratios provide that the free cylindrical area available for the flow of the exhaust gas out of the interspace between the exhaust gas duct 12 and the hemisphere 44 is larger than the outflow area of the exhaust gas duct 12, whereby the pressure drop is kept small, and provide that the distance remains small enough to produce a distinct radially outward flow deflection at the hemisphere 44 so that the exhaust gas flow is pressed into the air flow, whereby turbulences are produced. The space available for the flow of the exhaust gas/air mixture is additionally kept adequately large by keeping the cylindrical area between the orifice 34 and the hemisphere 44 approximately as large as the free-flow cross section parallel to the center axis at the level of the hemisphere 44 so that here, too, no excessive pressure losses occur. In this region, the exhaust gas/air mixture flow containing swirls is again directed radially inwards by the orifice 34, whereby swirls in the opposite direction are produced which finally lead to turbulences providing a very good mixing. These turbulences are maintained at a certain distance behind the orifice 34. This region in which the exhaust gas flows into the air and is mixed with the latter defines the mixing zone 36.

The hemisphere 44 further comprises a central hole 46 which prevents the occurrence of a stagnation point and thus also prevents a further pressure loss. The surface of the hemisphere 44 is electropolished on its side facing the flow and covered by a heating film on its opposite side such that condensation of exhaust gas is prevented. The hemisphere 44 is fastened to the orifice 34 via three braces 48 such that the hemisphere 44 can be preassembled with the orifice 34 in a simple manner and together with the orifice 34 be inserted concentrically to the dilution tunnel 38 into the latter. This flow deflection device 32 and its arrangement in the duct 20 provide that the exhaust gas flow is deflected symmetrically to the center axis, whereby a uniform mixing with the air is ensured.

Figure 3:
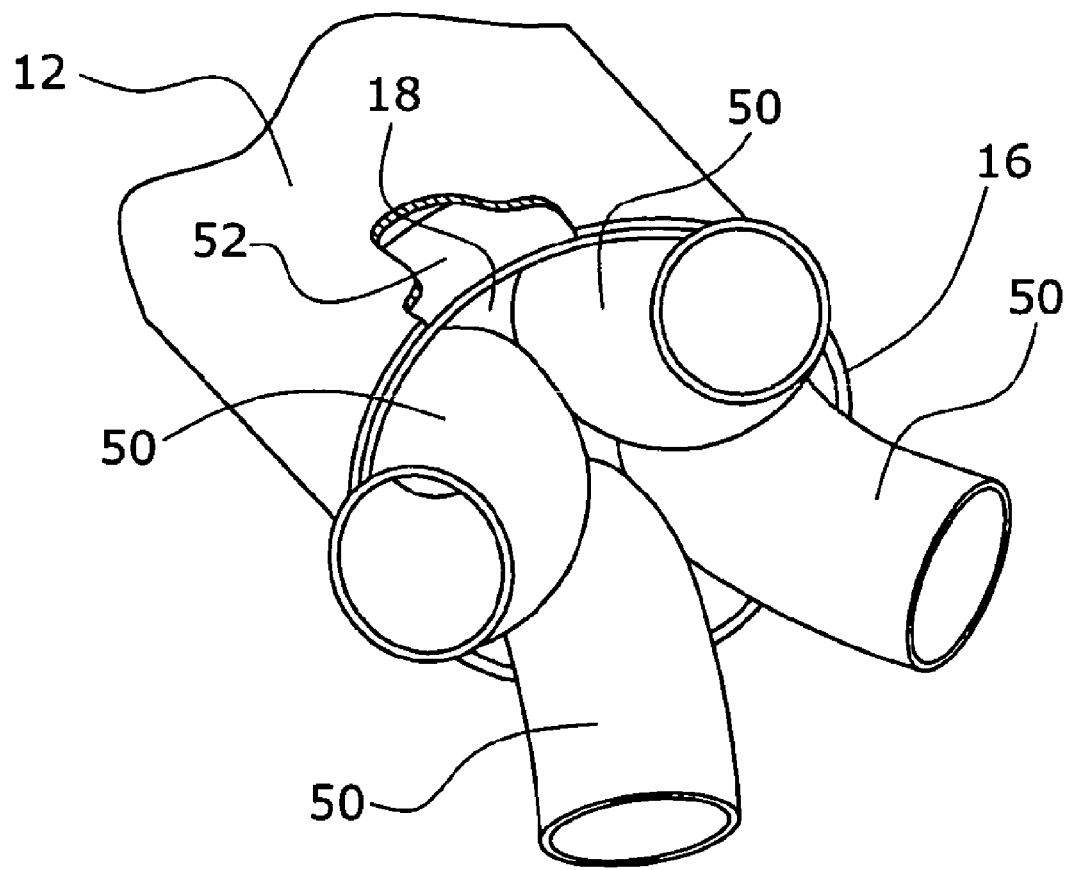
FIG. 3 shows a three-dimensional view of an alternative embodiment of the mixing zone.

FIG. 3 shows an alternative embodiment of the flow deflection device 32. In the outflow cross section 18 of the exhaust gas duct 12, four outflow pipes 50 arranged symmetrically to each other and offset 90° are located which at first extend in parallel to the flow direction of the exhaust gas duct 12 and are then bent radially outwards behind the end 16 of the exhaust gas duct 12 so that the pipes 50 in their course in the flow direction continuously depart from the center axis. The discharge cross sections of the outflow pipes 50 include an angle of 45° to the center axis of the dilution tunnel 38. These outflow pipes 50 are fastened in advance to a ring 52 which is fastened to the exhaust gas duct 12 during installation. Fastening to the orifice 34 via braces is also feasible.

This design of the flow deflection device 32 also provides for a flowing of the exhaust gas flow at an angle into the air flow in an axially symmetrical manner so that a radial component is imposed on the exhaust gas flow which leads to swirls being produced in a direction opposite to that of the swirls produced by the area reduced by the orifice 34 so that large turbulences occur, which result in very good mixing of the two gas flows. The continuous deflection provides for small pressure losses.

Both embodiments are accordingly suitable for an improved mixing and for homogenization of the exhaust gas flow so that a representative sampling is possible. This leads to better test results during analysis of the pollutant load without the need to increase the capacity of the feed pumps since existing pressure losses are kept as small as possible.

The present invention is not limited to embodiments described herein; reference should be had to the appended claims.

What is claimed is:

1. A system for taking an exhaust gas sample from an internal combustion engine, the system comprising:

an exhaust gas duct comprising an outflow cross section and an exhaust gas inlet, the exhaust gas duct being configured to be in a fluid communication with an exhaust gas source via the exhaust gas inlet;

an air duct configured to take in ambient air via an air filter, the outflow cross section of the exhaust gas duct being arranged so as to be substantially concentric in the air duct;

a mixing zone arranged downstream of the outflow cross section;

a dilution tunnel comprising a center axis, the dilution tunnel being configured to have an exhaust gas/air mixture flow therethrough;

a ring-shaped flow restrictor comprising an inner edge which defines exactly one orifice and an outer edge which is connected to the dilution tunnel, the ring-shaped flow restrictor being arranged downstream of the outflow cross section in the dilution tunnel via the outer edge so that each of the inner edge and the outer edge are concentric with the center axis of the dilution tunnel; and a flow deflection device arranged upstream of the ring-shaped flow restrictor and downstream of the outflow cross section, the flow deflection device being configured to deflect the exhaust gas/air mixture so that a flow of the exhaust gas/air mixture departs from the center axis of the dilution tunnel immediately downstream of the flow deflection device in an axially symmetrical manner, wherein the flow deflection device comprises a body comprising a spherical zone which is arranged so as to be substantially concentric in the dilution tunnel.

2. The system as recited in claim 1, wherein the spherical zone is a hemisphere.

3. The system as recited in claim 1, wherein the spherical zone is electropolished.

4. The system as recited in claim 1, wherein the spherical zone comprises a central hole.

5. The system as recited in claim 1, wherein at least one of the spherical zone and the ring-shaped flow restrictor is configured to be heated.

6. The system as recited in claim 5, further comprising a heating film, wherein the spherical zone comprises a downstream surface, the heating film being arranged on the downstream surface of the spherical surface or on the ring-shaped flow restrictor.

7. The system as recited in claim 1, wherein the spherical zone comprises a projection surface arranged in a direction of the center axis, the size of the projection surface corresponding at least to a size of the outflow cross section.

8. The system as recited in claim 1, wherein the ring-shaped flow restrictor comprises a flow cross section, and the flow deflection device comprises a cross section, the flow cross section of the ring-shaped flow restrictor being 1.2 to 1.8 times larger than the cross section of the flow deflection device.

9. The system as recited in claim 1, wherein a distance of the flow deflection device to the outflow cross section is ⅓ to ⅕ of a difference between a diameter of the air duct and a diameter of the exhaust gas duct.

10. The system as recited in claim 1, wherein a distance of the flow deflection device to the ring-shaped flow restrictor is ⅓ to ⅕ of a diameter of the air duct.

11. The system as recited in claim 1, further comprising at least one brace configured to fasten the flow deflection device to the ring-shaped flow restrictor.

12. The system as recited in claim 11, wherein the at least one brace comprises three braces which are configured to fasten the flow deflection device to the ring-shaped flow restrictor.

13. A system for taking an exhaust gas sample from an internal combustion engine, the system comprising:

an exhaust gas duct comprising an outflow cross section and an exhaust gas inlet, the exhaust gas duct being configured to be in a fluid communication with an exhaust gas source via the exhaust gas inlet;

an air duct configured to take in ambient air via an air filter, the outflow cross section of the exhaust gas duct being arranged so as to be substantially concentric in the air duct;

a mixing zone arranged downstream of the outflow cross section;

a dilution tunnel comprising a center axis, the dilution tunnel being configured to have an exhaust gas/air mixture flow therethrough;

a ring-shaped flow restrictor comprising an inner edge which defines exactly one orifice and an outer edge which is connected to the dilution tunnel, the ring-shaped flow restrictor being arranged downstream of the outflow cross section in the dilution tunnel via the outer edge so that each of the inner edge and the outer edge are concentric with the center axis of the dilution tunnel; and a flow deflection device arranged upstream of the ring-shaped flow restrictor and downstream of the outflow cross section, the flow deflection device being configured to deflect the exhaust gas/air mixture so that a flow of the exhaust gas/air mixture departs from the center axis of the dilution tunnel immediately downstream of the flow deflection device in an axially symmetrical manner, wherein, the flow deflection device comprises a plurality of outflow pipes arranged symmetrically to each other relative to the center axis.

14. The system as recited in claim 13, wherein the plurality of outflow pipes comprises four outflow pipes arranged so as to be offset from each other by 90°.

15. The system as recited in claim 14, wherein the four outflow pipes are arranged in a vicinity of the exhaust gas duct or in the exhaust gas duct, the four outflow pipes being arranged so as to first extend parallel to the center axis and, downstream of the exhaust gas duct, to continuously bend away from the center axis.

16. The system as recited in claim 13, wherein the plurality of outflow pipes each comprises a discharge cross section which is arranged at an angle of 30° to 80° with respect to the center axis.

* * * * *